United States Patent [19]

Woods, Jr.

[11] Patent Number: 5,108,365

[45] Date of Patent: Apr. 28, 1992

[54] TRANSLUMINAL INFUSION OF MAGNESIUM DURING CORONARY ANGIOPLASTY

[76] Inventor: Walter T. Woods, Jr., R.R. 1, Box 13, Chatham, Ill. 62629

[21] Appl. No.: 540,856

[22] Filed: Jun. 20, 1990

[51] Int. Cl.$^5$ .......................................... A61M 31/00
[52] U.S. Cl. ....................................................... 604/53
[58] Field of Search ................................ 604/96–103, 604/52, 53; 606/192, 194

[56] References Cited

U.S. PATENT DOCUMENTS

| | | | |
|---|---|---|---|
| 4,299,226 | 11/1981 | Banka | 604/52 |
| 4,376,117 | 3/1983 | Godfraind et al. | |
| 4,512,762 | 4/1985 | Spears | 604/21 |
| 4,531,936 | 7/1985 | Gordon | 604/52 X |
| 4,651,738 | 3/1987 | Demer et al. | |
| 4,773,899 | 9/1988 | Spears | 604/96 X |
| 4,777,951 | 10/1988 | Cribier et al. | |
| 4,799,479 | 1/1989 | Spears | |
| 4,824,436 | 4/1989 | Wolinsky | 604/53 |
| 4,975,279 | 12/1990 | Schumacher | 514/381 X |
| 5,008,284 | 4/1991 | Grover | 514/423 |

OTHER PUBLICATIONS

Anjani Dubey, et al., *Magnesium, Myocardial Ischaemia and Arrhythmias*, Drugs, vol. 37, pp. 1–7 (1989).

N. Ferrara et al., *Electrical and Mechanical Actions of Magnesium Sulfate During Ischemia and Reperfusion on Isolated Perfused Rat Heart*, Arch. Int. Pharmacodyn, vol. 293, pp. 84–96 (1988).

George E. Billman et al., *Prevention of Ventricular Fibrillation with Magnesium Sulfate*, European Journal of Pharmacology, vol. 158, pp. 167–171 (1988).

H. Sandvad Rasmussen et al., *Intravenous Magnesium in Acute Myocardial Infarction*, The Lancet, pp. 234–236, Feb. 1, 1986.

L. F. Smith et al., *Intravenous Infusion of Magnesium Sulphate After Acute Myocardial Infarction: Effects on Arrhythmias and Mortality*, International Journal of Cardiology, vol. 12, pp. 175–180 (1986).

Celia Chang et al., *Magnesium Deficiency and Myocardial Infarct Size in the Dog*, JACC, vol. 5, No. 2, pp. 280–289, Feb. 1985.

Burton M. Altura, *Ischemic Heart Disease and Magnesium*, Mini Reviews, Magnesium, vol. 7, pp. 57–67 (1988).

Bernard Horn, *Magnesium and the Cardiovascular System*, Magnesium, vol. 6, pp. 109–111 (1987).

Barbara Chipperfield et al., *Magnesium and the Heart*, American Heart Journal, vol. 93, No. 6, pp. 679–682 (1977).

B. M. Altura, *Sudden-Death Ischemic Heart Disease and Dietary Magnesium Intake: Is the Target Site Coronary Vascular Smooth Muscle?*, Medical Hypotheses, vol. 5, No. 8, pp. 843–848 (1979).

(List continued on next page.)

Primary Examiner—Edward M. Coven
Assistant Examiner—Sebastiano Passaniti
Attorney, Agent, or Firm—Hill, Van Santen, Steadman & Simpson

[57] ABSTRACT

Provided is an improved method of percutaneous transluminal balloon coronary angioplasty for dilating a narrowed portion of an artery. According to the method a multi-lumen inflatable balloon catheter having a predetermined balloon size and shape when inflated is introduced into the lumen of an artery in the patient and advanced until it is in the region of arterial narrowing. The balloon is then inflated for a pre-determined amount of time. According to a preferred embodiment the balloon is inflated for from about 1 to about 5 minutes. The inflated balloon deforms the adjacent narrowed portion of the artery and, in doing so, also blocks the blood flow through the artery. Into the lumen of the artery, immediately past the blockage created by the inflated balloon, an effective amount of a pharmaceutically acceptable magnesium preparation is then injected.

24 Claims, 4 Drawing Sheets

OTHER PUBLICATIONS

Prasad, D. M. V. Turlapaty et al., *Magnesium Deficiency Produces Spasms of Coronary Arteries: Relationship to Etiology of Sudden Death Ischemic Heart Disease*, Science, vol. 208, pp. 198–200 (1980).

Dan Tzivoni, et al., *Magnesium Therapy for Torsades de Pointes*, The American Journal of Cardiology, vol. 53, pp. 528–530 (1984).

Leon F. Kraft, et al., *Attenuation by Magnesium of the Electrophysiologic Effects of Hyperkalemia on Human and Canine Heart Cells*, The American Journal of Cardiology, vol. 45, pp. 1190–1191 (1980).

W. Thomas Woods, et al., *Electrophysiological Effects of Magnesium on Cells in the Canine Sinus Node and False Tendon*, Circulation Research, vol. 44, p. 183 (1979).

R. E. Katholi, et al., *Dual Dependence on Both $Ca^{2+}$ and $Mg^{2+}$ for Electrical Stability in Cells of Canine False Tendon*, Journal of Molecular and Cellular Cardiology, vol. 11, pp. 436–437 (1979).

W. T. Woods, et al., *Preservation of Resting Potential by Magnesium in Hypoxic Canine Cardiac Cells*, Magnesium, vol. 4, pp. 96–97 (1985).

S. Bloom, *Effects of Magnesium Deficiency on the Pathogenesis of Myocardial Infarction*, Magnesium, vol. 5, pp. 154–164 (1986).

Bjarne Bo Jeppesen, *Magnesium Status in Patients with Acute Myocardial Infarction: A Pilot Study*, Magnesium, vol. 5, pp. 95–100 (1986).

Irshad H. Chaudry, et al., *The Role of ATP-Magnesium in Ischemia and Shock*, Magnesium, vol. 5, pp. 211–220 (1986).

Ronald J. Korthuis et al., *Vascular Injury in Dogs During Ischemia-Reperfusion: Improvement with ATP-MgCl2 Pretreatment*, The American Physiological Society, pp. H702–H708 (1988).

Makoto Sunamori, et al., *Effect of Magnesium in Cardioplegic Solution Upon Hypothermic Ischemic Myocardial Mitochondria*, Japanese Circulation Journal, vol. 44, pp. 81–86 (1980).

TRANSLUMINAL INFUSION OF MAGNESIUM DURING CORONARY ANGIOPLASTY

BACKGROUND OF THE INVENTION

1. Field of the Invention

The present invention relates to percutaneous transluminal coronary angioplasty, and more particularly to a method for alleviating the myocardial ischemia generally associated with angioplasty.

2. Description of the Prior Art

Arteriosclerosis is a general term which refers to any pf a group of diseases in which the lumen of an artery becomes narrowed or blocked. The most common and important form of arteriosclerosis is the disease known as atherosclerosis. In atherosclerosis, material accumulates in the inner layer of an artery, narrowing of the arterial lumen. This, in turn, restricts the flow of blood through the artery. In fact, the flow of blood can become so restricted that it hinders the functioning of, or permanently damages, the organ which the artery feeds. These accumulations of material will hereinafter be referred to synonymously as lesions, plaques, or atheromas.

Atherosclerosis is treated by alleviating the diminished blood flow. This can often be accomplished by pharmacological therapy. For example, certain pharmacologicals can dilate the lumen of an affected artery, thereby restoring adequate blood flow. However, in most cases surgery is required to reestablish a lumen of proper diameter. A number of surgical procedures have been developed to this end. However, these procedures, such as arterial by-pass grafts, are major surgical operations, and accordingly, present a number of disadvantages to a patient, i.e., financial costs, inconvenience, discomfort, permanent disfigurement, and the risk of complications associated with any major surgery. In light of these disadvantages, methods of re-establishing proper lumen diameter in an occluded artery have been recently developed which are relatively non-invasive and present less risk to a patient than conventional surgery.

One such method is percutaneous transluminal coronary angioplasty, hereinafter referred to as angioplasty. Generally, angioplasty is preformed using a multi-lumen inflatable balloon catheter. At least one lumen of the catheter is open-ended allowing the passage of a guide-wire, or in some instances, the direct intra-arterial infusion of pharmacological agents. According to the procedure, the guide-wire is directed to the area of arterial narrowing using x-ray monitoring. Thereafter, the catheter is positioned, with the aid of the guide-wire, in the region of arterial narrowing. Concentric with the lumen including the guide-wire is a second lumen which connects to an elongated inflatable segment, or balloon portion, near the distal end of the catheter. The second lumen and balloon are generally filled with diluted contrast medium. The contrast medium is a radio-opaque liquid which makes visualization of the catheter possible by means of fluoroscopy.

Typically, the procedure for angioplasty involves first selecting a convenient place to introduce the catheter into the arterial system of the patient, for example, the femoral artery of the leg. Next, the catheter is guided to the affected artery, for example, the left anterior descending coronary artery. This is done manually with the aid of fluoroscopy. When the catheter is appropriately positioned, the guide-wire is advanced to and passed through the point of obstruction. The balloon catheter, which surrounds the guide-wire, is then advanced along the guide wire until it is surrounded by the occluding atheroma. The balloon, which is constructed of material having a high tensile strength and low elasticity, is then inflated. As the balloon expands it deforms the occluding atheroma adjacent to its surface. This creates a larger inner diameter within the occluded artery. The usual method is to repeat the inflation an arbitrary number of times. It is hoped that by repeatedly deforming the occluding atheromas they will become permanently deformed, thus providing the affected artery with a lumen having a sufficient inner diameter. Further, it is believed that by prolonging the rate that the balloon is inflated reduces the possibility of re-stenosis. By reducing the rate at which the balloon is inflated, the atheroma is slowly stretched and deformed, it is believed that the combination of these actions reduces the likelihood of re-stenosis. The balloon is then collapsed and retracted. The site of the obstruction is then examined angiographically. This is often accomplished by injecting a radio-opaque dye through lumen housing the guide-wire. If the artery is still occluded, the procedure is repeated.

Standard angioplasty protocol requires that the balloon is inflated for a period of about 60 seconds. During this period, the flow of blood through the artery is blocked, and the supply of blood perfusing tissue past the blockage becomes inadequate to sustain cellular metabolism, a condition known as ischemia. If the ischemic episode is prolonged, the affected tissue will die, a condition known as infarction. For example, when angioplasty is performed to reduce an $ occlusion in a coronary artery, e.g., percutaneous transluminal coronary angioplasty, myocardial tissue downstream from the inflated balloon becomes ischemic. The extent of damage to the myocardial tissue and the morbidity of the corresponding pathological syndrome depends greatly on the length of time the blood flow is interrupted. Symptomatic o myocardial ischemia caused by angioplasty are characteristic severe chest pain and electrocardiogram (ECG) changes, e.g., ST segment elevation. Further, if the ischemic episode is not promptly resolved, infarction, dysrhythmia, and possibly death will occur.

Because of the accompanying pain and possibility of infarction and dysrhythmia, present angioplasty procedures only allow the balloon to remain inflated for about 60–120 seconds. Since the balloon remains inflated for such a short period of time, the procedure is very inefficient, and the inflation of the balloon must be repeated several times. Further, repeated inflations increase the likelihood of re-stenosis. In order to increase the efficiency of the procedure and decrease the likelihood of re-stenosis, it would be advantageous to prolong the balloon inflation time. A method to prolong balloon inflation time while at the same time decreasing patient pain and risk of complications would be a substantial improvement over present state-of-the-art percutaneous transluminal coronary angioplasty procedures.

SUMMARY OF THE INVENTION

Ischemia is the pathological state in which blood flow is inadequate to meet tissue oxygen demands. During a coronary angioplasty procedure major coronary arteries are blocked. This temporarily interrupts the flow of blood. When the supply of oxygen-rich blood is interrupted, the oxygen-deprived tissues becomes ischemic. The effects of myocardial ischemia are numerous and include, but are not limited to: electrical instability; spontaneous membrane depolarization of the myocytes; the appearance of ectopic ventricular beats possibly leading to ventricular fibrillation; rapid impairment of cardiac contractility; rapid depletion of cellular ATP levels; cell death; tissue necrosis; patient pain; and occasionally patient death. The extent of morbidity and mortality during an ischemic episode is generally a function of time, i.e., the longer myocardial tissues are deprived of oxygen, the greater the risk of dysrhythmia, permanent damage to the heart, or death.

One of the major problems with percutaneous transluminal coronary angioplasty is that there has heretofore been no means to prevent or alleviate the myocardial ischemia associated with the procedure. Thus, balloon inflation time has been limited to very short periods of time, usually ranging from about 60 to about 120 seconds. This has resulted in the establishment of arbitrary protocols whereby the balloon is inflated repeatedly an arbitrary number of times. However, this protocol results in a direct risk to the patient since each balloon inflation represents a risk of balloon rupture. Further, each balloon inflation stresses and damages the walls of the affected artery, which translates into subsequent re-stenosis, or worse, an aneurism or rupture of the arterial wall.

It is therefore a principle object of the present invention to provide an improved method for percutaneous transluminal coronary angioplasty. It is a further object of the present invention to provide an improved method of percutaneous transluminal coronary angioplasty which includes a prolonged balloon inflation time. It is still a further object of the present invention to provide an improved method of percutaneous transluminal coronary angioplasty which minimizes the pain and risk of complications to the patient.

The objects set forth above and others are accomplished by the present invention which provides an improved method for percutaneous transluminal coronary angioplasty. The method comprises a balloon inflation time substantially longer in duration than present state-of-the-art protocols without the deleterious effects of ischemia which would normally be expected. Accordingly, one aspect of the present invention is directed to a method of percutaneous transluminal coronary angioplasty for dilating a narrowed portion of an artery. According to the method, a multi-lumen inflatable balloon catheter having a pre-determined balloon size and shape when inflated is provided. The catheter is introduced into the lumen of an artery in the patient, and advanced until it is in the region of arterial narrowing. The balloon is then inflated for a pre-determined amount of time. According to a preferred embodiment the balloon is inflated for from about 1 to about 5 minutes. The inflated balloon deforms the adjacent narrowed portion of the artery and, in doing so, also blocks the blood flow through the artery. Into the lumen of the artery, immediately past the blockage created by the inflated balloon, an effective amount of a pharmaceutically acceptable magnesium preparation is then injected.

According to one embodiment of the invention a multilumen inflatable balloon catheter having an inflatable balloon portion and an opening distal to the inflatable balloon portion through which fluids may be injected is provided. The balloon catheter is then introduced into the lumen of an artery in the patient, and advanced until the catheter is in the region of arterial narrowing such that the inflatable balloon portion is adjacent to the region of arterial narrowing and the distal opening is advanced past therefrom. The balloon portion is then inflated for from about 1 to about 5 minutes. The inflated balloon portion deforms the adjacent narrowed portion of the artery and, in doing so, also blocks the blood flow through the artery. Through the distal opening of the catheter and into the lumen of the artery is injected from about 10 nanomoles to about 1.0 micromole per Kg body weight per minute of a pharmaceutically acceptable magnesium preparation. The balloon portion is then deflated, and through the distal opening of the catheter a radio-opaque contrast dye is injected into the area of arterial narrowing. A fluoroscopic angiogram shows if an acceptable lumen diameter has been restored. If the coronary angiogram demonstrates that the narrowed portion of the artery is not sufficiently deformed, the method is repeated until a proper lumen diameter is restored as demonstrated by angiography. The catheter is then removed from the patient.

BRIEF DESCRIPTION OF THE DRAWINGS

Other objects and advantages of the invention will become apparent upon reading the following detailed description and upon reference to the drawings in which:

FIG. 8 is the first in a series of electrocardiograms (ECG) from one patient undergoing percutaneous transluminal coronary angioplasty. FIG. 8 is the control EKG obtained prior to the angioplasty procedure.

DESCRIPTION OF THE PREFERRED EMBODIMENTS

In accordance with the present invention, the objects set forth above are accomplished by the present invention which provides an improved method for percutaneous transluminal coronary angioplasty. The method comprises a balloon inflation time substantially longer in duration than present state-of-the-art protocols without the deleterious effects of ischemia which would normally be expected.

Experiments with the present invention demonstrate that magnesium infused intraarterially past the point of coronary obstruction prevents or delays the occurrence of ischemia in oxygen-deprived tissues. Generally, when the flow of blood through an artery is stopped, the tissues perfused by that artery become ischemic and may die. However, surprisingly, the present invention prevents or delays these tissues from becoming ischemic. Thus, it has been unexpectedly determined that magnesium is cardio-protective during ischemic episodes and may advantageously be utilized in angioplasty procedures.

According to one embodiment of the invention, an inflatable balloon catheter is introduced into the lumen of an artery in the patient. Balloon catheters useful in the present invention preferably provide a conduit for injecting fluids past the point of obstruction (balloon inflation). It should be noted, however, that any means for injecting a magnesium preparation past the point of obstruction in an artery is contemplated by the present invention, e.g., hypodermic injection, intra-coronary catheterization, or the like. Nevertheless, balloon catheters which include a lumen for injecting fluids past the point of obstruction are common in the industry and may be used in the practice of the present invention. Generally, the lumen through which fluids are injected is the same lumen through which a guide-wire for positioning the catheter is inserted. Examples of balloon catheters useful in the practice of the present invention include, but are not limited to, Medtronic Thruflex or Advanced Cardiovascular Systems No. 8 catheters.

The catheter is advanced until it is in the region of arterial narrowing. The balloon of the catheter has a predetermined size and shape. Physicians often choose these catheters by the diameter of the arterial lumen being treated. The balloon is then inflated for a predetermined amount of time. According to a preferred embodiment the balloon is inflated for from about 1 to about 5 minutes. According to a further preferred embodiment, the balloon remains inflated for about 2 to about 4 minutes, and most preferably, about 3 minutes. The rate of balloon inflation and deflation is preferably slow so that the maximum amount of stretch is achieved in the atheroma. For example, according to one embodiment, the balloon is inflated over a period of one minute, and deflated over a subsequent period of one minute.

The inflated balloon deforms the adjacent narrowed portion of the artery and, in doing so, also blocks the blood flow through the artery. Into the lumen of the artery, immediately past the blockage created by the inflated balloon, an effective amount of a pharmaceutically acceptable magnesium preparation is then injected. Magnesium is a mineral essential for almost every biological process including glucose metabolism, protein and nucleic acid synthesis, electrical balance of cells, and the transmission of nerve impulses. The present invention also demonstrates that magnesium is useful in preventing the ischemia generally associated with coronary blockage. Preferably, the pharmaceutically acceptable magnesium preparation is a sterile solution including one or more magnesium salts. Any sterile solution in which the magnesium salt is soluble may be used to deliver the magnesium to the site of ischemia. For example, the sterile solutions include, but are not limited to, 5% dextrose in water, Ringer's injection, and 0.9% saline in water.

Referring to the magnesium salt included in the preparation, the magnesium salt is preferably any salt of magnesium which disassociates to form ionic magnesium in water. Preferable magnesium salts include the sulfate, gluconate and chloride. The most preferable salt is the chloride. Nevertheless, without limiting the invention, it is believed that the disassociated magnesium ion provides the therapeutic benefit of the preparation, and accordingly, all non-toxic magnesium salts, complexes and other preparations which release ionic magnesium into an aqueous solution are within the contemplation of the present invention.

The magnesium preparation is administered in an effective amount. Preferably, the effective amount of magnesium administered is from about 10 nanomoles to about 1.0 micromole/Kg minute. More preferably, the effective amount of magnesium administered is from about 50 to about 500 nanomole/Kg/minute. Most preferably, the effective amount of magnesium is about 100 nanomoles/Kg/minute. In accordance with one embodiment of the invention, the effective amount of magnesium is infused directly into the coronary artery being treated over an extended period of time.

Once the balloon is deflated a radio-opaque contrast dye may be injected into the area of arterial narrowing, and a coronary angiogram is performed. If a proper lumen diameter has been re-established, the catheter is removed. If, however, a proper diameter has not been re-established, the above-described procedure is repeated.

By prolonging or slowing balloon inflation time, atheromas occluding the lumen of the affected artery can be compressed or stretched for an extended period, thereby diminishing the likelihood of re-stenosis. Moreover, prolonging or slowing the period of balloon inflation reduces the necessity of repeated balloon inflation, thereby reducing the risk of the balloon or the artery rupturing and the likelihood of re-stenosis. In the examples described below, experiments with the present invention show that magnesium prevents damage to tissues deprived of oxygen for extended periods of time. Accordingly, the inventive method does more than provide for extended balloon inflation time, it protects the cardiac muscle form the deleterious effects of ischemia during the angioplasty procedure.

The following examples are presented to describe preferred embodiments and utilities of the invention and are not intended to limit the invention unless otherwise stated in the claims appended hereto.

EXAMPLES

EXAMPLE 1

CARDIOPROTECTIVE EFFECT OF MAGNESIUM INFUSION DURING PERIODS OF PROLONGED ISCHEMIA

Adult mongrel dogs (21±/− 3 kg., either sex) were anesthetized with pentobarbital sodium (30 mg/kg., intravenous) and ventilated (Harvard Respirator) via a thoracotomy. Chests were opened in the left third intercostal space. Hearts were supported by pericardial cradle to present access to the proximal left anterior descending (ventral interventricular) coronary artery. Catheters were inserted in the femoral vein for general infusion and the femoral artery for aortic pressure measurements. Electrocardiograph (ECG) needle leads were inserted into limbs to record ECGs. Unipolar silver electrodes were embedded 2.0 mm deep in ventral ventricular muscle in the area predicted to be at risk. This lead substituted for the chest lead in the standard ECG to register local electrophysiologic changes associated with ischemia.

A 19 gauge polypropylene catheter was inserted in the proximal left anterior descending (LAD) artery. Care was taken to leave septal artery perfusion intact. The LAD artery was occluded with a snare around it tightened around the catheter which served as the route of administration for test agents during the occlusion period.

To screen for responsiveness to LAD occlusion, the snare was tightened to the point of 100% occlusion for 5-minutes and then released. Only those experiments were included in the study which satisfied all the following criteria, with the exception of #5), within the five-minute occlusion:

1. ST segment change in a limb lead exceeded 0.2 mv.
2. Mean arterial pressure fell by at least 20 mm Hg.
3. Epicardial surface wall motion visibly decreased.
4. Color of epicardial muscle in the occluded zone became different from that of surrounding tissue.
5. All above changes were reversed within 10 min. after return of the artery to 0% occlusion.

Once the above criteria were satisfied, the LAD of each dog was completely occluded for three hours. Throughout the period of occlusion, sterile Ringer's injection solution obtained from Baxter Healthcare Corporation, Deerfield, Ill., was continuously infused into LAD lumen at a point just past the point of occlusion, at the rate of 0.4-0.8 ml./min. In one group including six dogs, the Ringer's injection was not supplemented. In a second group including eight dogs, the Ringer's injection was supplemented with magnesium chloride. The magnesium chloride brought the infusion Mg concentration to 8.0 mmol./l. Throughout the occlusion period, the flow rate of the infusion through the LAD lumen was maintained constant for both groups.

After the three hour occlusion period concluded, all the dogs were sacrificed and the hearts were removed and prepared to determine the amount of infarction suffered. The amount of infarction suffered during the three hour occlusion was determined using a tetrazolium stain technique. According to that technique, coronary artery ostia were infused with 100 ml of 25° C. normal saline to rinse most of the blood from the hearts. Right ventricles and atria were excised leaving only left ventricles at 25° C. These were transected in 1.0 cm slices from valve rings to apex. All slices were submerged in NBT (2%) at 30° C. and swirled gently. After 15 minutes slices were removed and blotted with absorbent tissue to dryness. Each was placed with its superior (cranial) surface in contact with a transparent sheet so that its epicardial and endocardial borders could be traced by hand. Dark blue to black portions of the tissue representing infarcted zones were also outlined by hand so the outlined area could be quantified (in cm2) by planimetry. Each slice was weighed after blotting so the infarct area could be converted to infarct mass in grams. Slices were stored in 10% formalin which enhanced the contrast between the infarcted and non-infarcted tissue. Measurements were compared to those obtained after 3 days in formalin. If the result were significantly different they were deleted from the study group. This corrected for misinterpretation of infarcted areas that were marginally stained before storage in formalin.

Referring to the results obtained in the group not receiving magnesium supplementation, rhythm disturbances, discoloration of tissue, and loss of wall motion within the first hour was seen in each dog tested. Three hearts arrested in ventricular fibrillation in less than 45 min. Nitro-blue tetrazolium stain revealed infarction of 55 +/− 12% of the left ventricular mass. Effects on percent infarction (49 ±/− 10%) in the 6 hearts tested were not significantly different ($P>0.05$) from those observed when no Ringer's was infused. In the three dogs which did not arrest in the group, cardiac rhythms remained stable throughout the 3-hour LAD occlusion. However, large changes ($P<0.05$) in ST segments were observed. Random premature ventricular contractions were observed in each dog with progressively greater frequency during the course of the occlusion period.

Referring to the group receiving a magnesium supplemented infusion, the LAD artery occlusion procedure was performed in 8 dogs with magnesium chloride supplementation initiated at the moment of artery occlusion. In all eight dogs ST segments remained unchanged from control ($P>0.05$) levels. Also, cardiac rhythms remained stable throughout the 3 hour postocclusion period. No magnesium treated dog experienced arrest or ventricular fibrillation during the study. NTB stain showed only 3 ±/− 5% infraction of the left ventricular mass ($P<0.05$) in the magnesium treated group. In contrast, the group which was not treated with a magnesium infusion suffered greater than 50% infarction.

Figure 1:
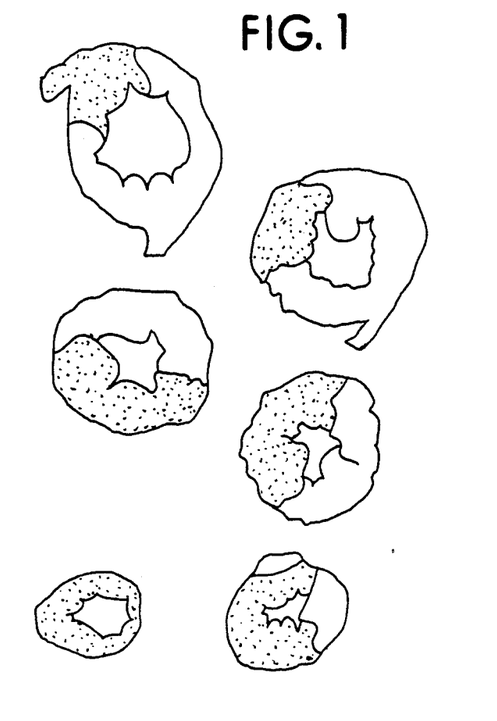
FIG. 1 is an illustration of six transverse left ventricular sections showing areas of infarction, areas unstained by nitro-blue tetrazolium, as shaded areas. These sections are from a dog not treated with magnesium.
Figure 2:
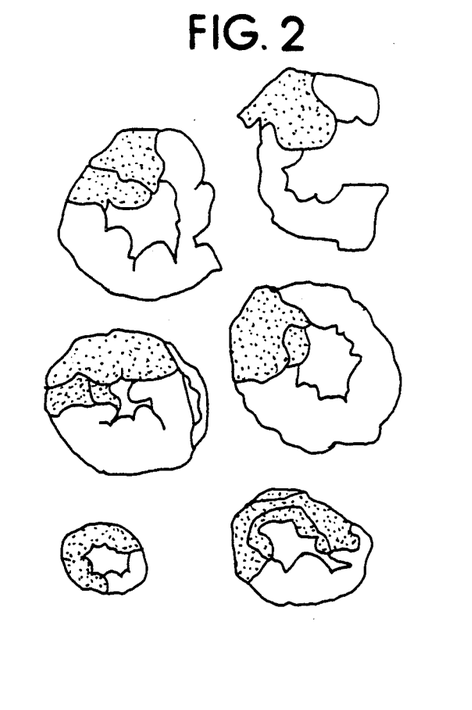
FIG. 2 is an illustration of six transverse left ventricular sections showing areas of infarction, areas unstained by nitro-blue tetrazolium, as shaded areas. These sections are from a dog not treated with magnesium.
Figure 3:
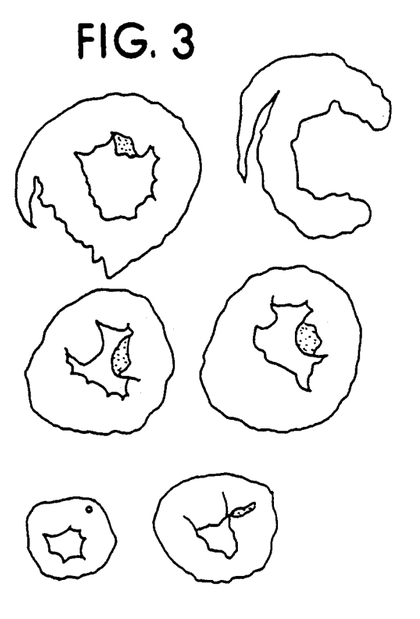
FIG. 3 is an illustration of six transverse left ventricular sections showing areas of infarction, areas unstained by nitro-blue tetrazolium, as shaded areas. These sections are from a dog treated with magnesium.
Figure 4:
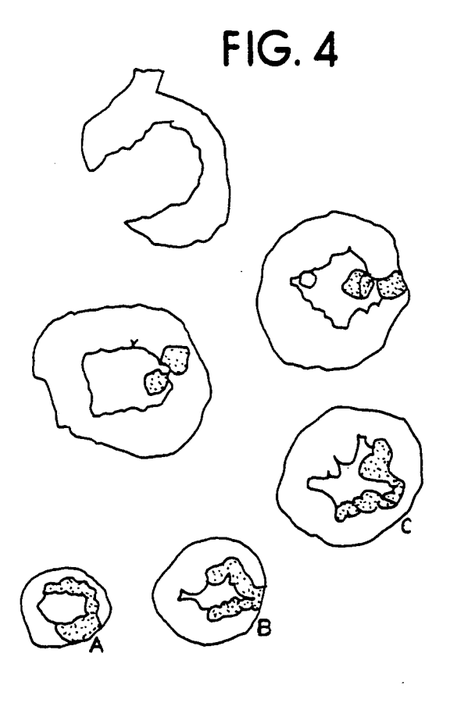
FIG. 4 is an illustration of six transverse left ventricular sections showing areas of infarction, areas unstained by nitro-blue tetrazolium, as shaded areas. These sections are from a dog treated with magnesium.
Figure 5:
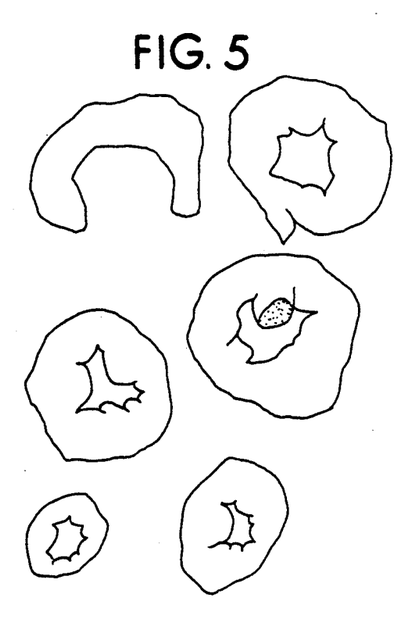
FIG. 5 is an illustration of six transverse left ventricular sections showing areas of infarction, areas unstained by nitro-blue tetrazolium, as shaded areas. These sections are from a dog treated with magnesium.
Figure 6:
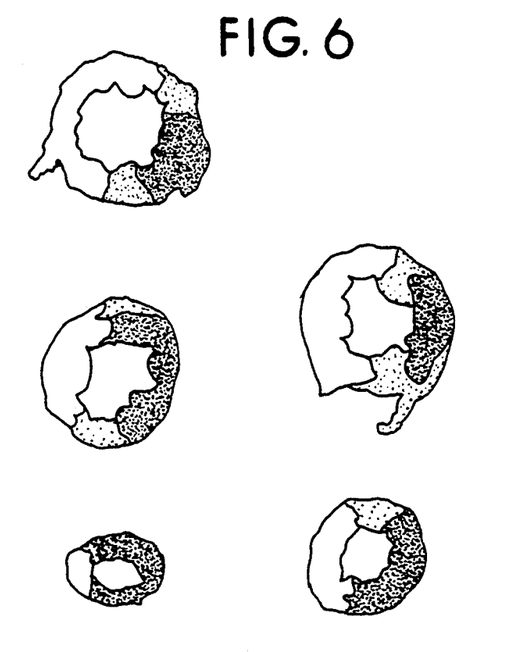
FIG. 6 is an illustration of six transverse left ventricular sections in which the regions perfused by the occluded artery are identified by post-occlusion injection with monastral red polymer. Infarcted areas are represented as black areas, and the remaining areas perfused by the occluded artery are represented as shaded areas. These sections are from a dog not treated with magnesium.
Figure 7:
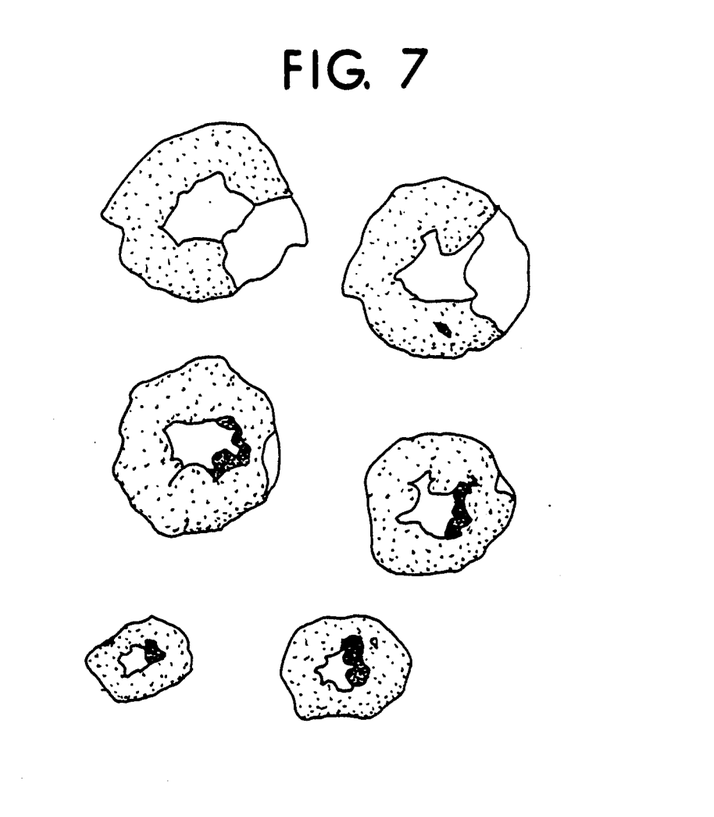
FIG. 7 is an illustration of six transverse left ventricular sections in which the regions perfused by the occluded artery are identified by post-occlusion injection with monastral red polymer. Infarcted areas are represented as black areas, and the remaining areas perfused by the occluded artery are represented as shaded areas. These sections are from a dog treated with magnesium.
Figure 8:
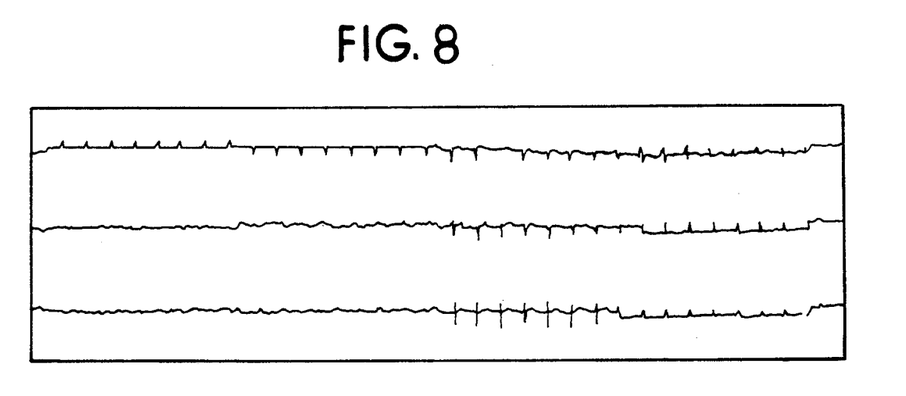
Figure 9:
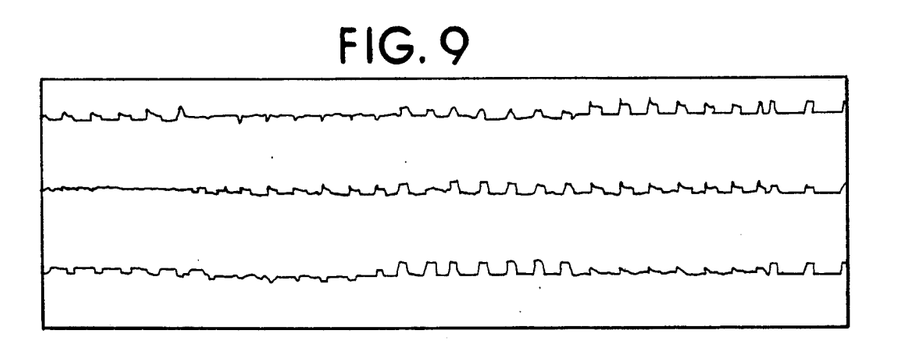
FIG. 9 is the ECG of the same patient obtained after 15 seconds of complete arterial occlusion by balloon inflation. Major changes in ST segment typical of myocardial ischemia appeared even within these brief periods of inflation.

Referring to the Figs., FIGS. 1 and 2 show that the three hour LAD occlusions produced infarction of over 49 ±/− 10% of the left ventricular mass in the group not receiving the magnesium supplemented infusion. FIGS. 3–6 show that the three hour occlusions only produced infarction mass of less than 10% of the left ventricular mass in the group receiving the magnesium supplemented infusion. Moreover, the magnesium-free group was accompanied by severe ST segment elevation, premature ventricular contractions, and arrhythmias. However, in the presence of magnesium ion, coronary artery occlusion produced only minor change in ST segment and negligible incidence of arrhythmias. These results show the cardio-protective affect of intracoronary infused magnesium during periods of prolonged ischemia.

EXAMPLE 2

CARDIOPROTECTIVE EFFECT OF MAGNESIUM DURING CORONARY ANGIOPLASTY

The following study was preformed using a human volunteer. The study demonstrated an improved method of percutaneous transluminal coronary angioplasty. More specifically, the study illustrated the utility of intracoronary magnesium infusion during balloon angioplasty procedures.

In a 60 year old male with coronary artery disease an angioplasty balloon catheter (Advanced Cardiovascular Systems, Inc. No. 8) was inserted into the femoral artery and advanced, using fluoroscopy to observe the advancing catheter, into the lumen of the proximal left anterior descending artery. The catheter included two lumens. One lumen, open at both ends, included a guide-wire for positioning the catheter, and one lumen included the inflatable balloon. The catheter was constructed such that when the balloon was inflated, fluids could be infused into the lumen of the occluded vessel past the point of occlusion. Catheters constructed in this manner are common throughout the industry.

Once the catheter was in position, Ringers' injection was infused through the balloon catheter past the point of occlusion into the lumen of the artery at a rate of 1.0 ml/minute. The infusion was administered by a Baxter infusion pump through the balloon catheter into the region of ischemia past the point of occlusion. The patient's comfort was monitored throughout the test. The patient's cardiac function was also continuously monitored by means of an electrocardiogram (ECG).

A control ECG was obtained prior to inflating the balloon. The balloon then was inflated. The inflated balloon completely obstructed the flow of blood through the artery. The balloon remained inflated for 15 seconds. Past the point of occlusion, the Ringer's injection was continually infused at a rate of 1.0 ml/minute. The downstream myocardium became progressively more ischemic until the balloon was deflated. This period of ischemia was accompanied by characteristic severe chest pain and characteristic ECG changes, e.g., ST segment elevation. An ECG, FIG. 11, was obtained at this time which shows these changes.

Magnesium chloride was then added to the infusion to a concentration of 8.0 micromole/liter. The infusion including the magnesium chloride was infused at a rate of 1.0 ml/minute continuously during this portion of the study. The balloon was then re-inflated. The balloon remained inflated for a period of over three minutes. An ECG, FIG. 12, was obtained after the artery had been occluded for 65 seconds. While the balloon was inflated, the patient experienced no chest pain and the ECG compared favorably with the control, non-stressed, ECG.

This procedure demonstrated that the intra-coronary infusion of magnesium eliminated the chest pain and ECG changes typically associated with the ischemia developed during coronary angioplasty. Further, the infusion of magnesium allowed balloon inflation time to be increased to about three minutes, 12 times as long as without administering magnesium.

Figure 10:
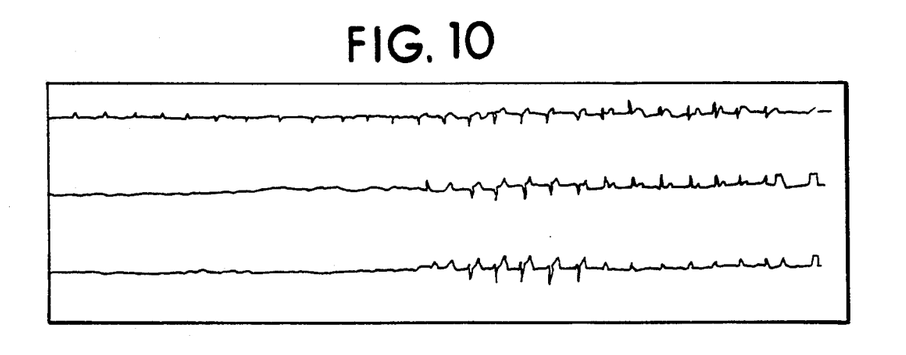
FIG. 10 is subsequent ECG of the same patient obtained while a magnesium solution was being infused within the coronary artery past the point of occlusion, after 65 seconds of complete arterial occlusion by balloon inflation. The ECG was unchanged from the control and the patient reported no chest discomfort.

FIG. 10 is the control electrocardiogram. FIG. 10 shows the normal, non-stressed, ECG of the patient. FIG. 11 is the electrocardiogram of the same patient after 15 seconds of complete arterial occlusion by balloon inflation. During this stage of the procedure the patient was continuously infused with Ringer's injection past the point of occlusion. Nevertheless, major changes in ST segment were noted. These changes are typical of myocardial ischemia. Further, the patient reported chest discomfort at this time. FIG. 12 is the ECG of the same patient during a subsequent second balloon inflation. FIG. 12 was obtained while magnesium supplemented Ringer's solution was being infused into the coronary artery past the point of obstruction. The ECG was obtained after 65 seconds of complete arterial occlusion by balloon inflation. Notably, the ECG was unchanged from the control (FIG. 10). Moreover, the patient reported no chest discomfort throughout the second inflation period. The balloon remained inflated for a period of 3 minutes. However, it is believed that the balloon inflation period may have been extended further without injuring or causing pain to the patient.

The above-described procedure was repeated in three other patients with coronary artery disease who underwent angioplasty. In each case, Mg supplementation prolonged the period of symptomless balloon inflation. No exceptions were observed.

While the invention is susceptible to various modifications and alternative forms, specific embodiments thereof have been shown by way of example and have herein been described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. A method of percutaneous transluminal coronary angioplasty, the method including the step of injecting into the lumen of an artery occluded by an inflated balloon of a balloon catheter, immediately past a blockage created by the inflated balloon and prior to any ischemia caused by the balloon, an effective amount of a pharmaceutically acceptable magnesium preparation to prevent or delay ischemia.

2. A method of percutaneous transluminal coronary angioplasty, the method including the steps of:
   (a) providing a multi-lumen inflatable balloon catheter having a pre-determined balloon size and shape when inflated;
   (b) introducing said catheter into the lumen of an artery in a patient;
   (c) advancing said catheter until said catheter is in a region of arterial narrowing;
   (d) inflating the balloon for a pre-determined amount of time whereby the inflated balloon blocks the flow of blood through the artery while it deforms an adjacent narrowed portion of the artery; and
   (e) injecting into the lumen of the artery, immediately past the blockage created by the inflated, balloon prior to any ischemia caused by the balloon, an effective amount of a pharmaceutically acceptable magnesium preparation to prevent or delay ischemia.

3. A method of percutaneous transluminal coronary angioplasty, the method including the steps of:
   (a) providing a multi-lumen inflatable balloon catheter having a pre-determined balloon size and shape when inflated;
   (b) introducing said catheter into the lumen of an artery in a patient;

(c) advancing said catheter until said catheter is in a region of arterial narrowing;

(d) inflating the balloon for a pre-determined amount of time from about one to five minutes whereby the inflated balloon blocks the flow of blood through the artery while it deforms an adjacent narrowed portion of the artery; and (e) injecting into the lumen of the artery, immediately past the blockage created by the inflated balloon, an effective amount of a pharmaceutically acceptable magnesium preparation.

4. The method of claim 2 wherein the method includes the additional steps of:
   (a) deflating and retracting the balloon;
   (b) injecting a radio-opaque contrast dye into the region of arterial narrowing;
   (c) preforming a coronary angiogram; and
   (d) removing the catheter from the patient.

5. The method of claim 2 wherein said pre-determined inflation time is from about two to about four minutes.

6. The method of claim 2 wherein said pre-determined inflation time is about three minutes.

7. The method of claim 1 or 2 wherein the magnesium preparation includes magnesium chloride.

8. The method of claim 1 or 2 wherein the magnesium preparation includes magnesium gluconate.

9. The method of claim 1 or 2 wherein the magnesium preparation includes magnesium sulfate.

10. The method of claim 1 or 2 wherein the effective amount of the pharmaceutically acceptable magnesium preparation injected includes from about 10 nanomoles to about 1.0 micromole/Kg/minute of magnesium.

11. The method of claim 1 or 2 wherein the effective amount of the pharmaceutically acceptable magnesium preparation injected includes from about 50 to about 400 nanomoles/Kg/minute of magnesium.

12. The method of claim 1 or 2 wherein the effective amount of the pharmaceutically acceptable magnesium preparation injected includes from about 75 nanomoles to about 200 nanomoles/Kg/minute magnesium chloride.

13. The method of claim 1 or 2 wherein the effective amount of the pharmaceutically acceptable magnesium preparation injected includes about 100 nanomoles/Kg/minute of magnesium.

14. A method of percutaneous transluminal coronary angioplasty for dilating a narrowed portion of a coronary artery in a patient in need thereof, the method including the steps of:
   a) providing a multi-lumen inflatable balloon catheter having an inflatable balloon portion and an opening distal from said inflatable balloon portion through which a guide-wire is threaded and fluids are injected;
   b) introducing said balloon catheter into the lumen of an artery in the patient;
   c) advancing said balloon catheter until said catheter is in a region of arterial narrowing such that the inflatable balloon portion is adjacent to the region of arterial narrowing and said distal opening is advanced past therefrom;
   d) inflating the balloon portion for from about 1 to about 5 minutes, said inflated balloon portion deforming the adjacent region of arterial narrowing and blocking blood flow through said artery;
   e) injecting through said distal opening into the lumen of the artery from about 10 nanomoles to about 1.0 micromole/Kg/minute of a pharmaceutically acceptable magnesium preparation;
   f) deflating the balloon portion;
   g) injecting into the region of arterial narrowing through said distal opening a radio-opaque contrast dye;
   h) performing a coronary angiogram;
   i) repeating steps d), e), f), g) and h) if said coronary angiogram demonstrates that said narrowed portion of the artery is not sufficiently deformed; and
   j) removing the catheter from the patient.

15. The method of claim 14 wherein said inflation time is further defined as about three minutes.

16. The method of claim 14 wherein the magnesium preparation includes magnesium chloride.

17. The method of claim 14 wherein the magnesium preparation includes magnesium gluconate.

18. The method of claim 14 wherein the magnesium preparation includes magnesium sulfate.

19. The method of claim 14 wherein the effective amount of the pharmaceutically acceptable magnesium preparation injected is further defined as including about 100 nanomoles/Kg/minute of magnesium.

20. A method of percutaneous transluminal coronary angioplasty for treating patients having atheromatous narrowing of a coronary artery, the method including the steps of:
   a) providing a multi-lumen inflatable balloon catheter, said catheter including a first lumen and second lumen, said first lumen having an inflatable balloon portion, said balloon portion having a diameter sufficient when inflated to deform the atheromas immediately adjacent an outer surface of the balloon, said second lumen defining a conduit to a distal tip of said catheter, said distal tip located distal the inflatable balloon portion; said distal tip including an opening through which a guide wire is threaded and fluids are injected;
   b) introducing said balloon catheter into the lumen of said coronary artery;
   c) advancing said catheter into a portion of said coronary artery narrowed by atheromas such that the outer surface of the inflatable balloon portion is positioned immediately adjacent the atheromas narrowing the artery and the distal tip of the catheter is positioned in the lumen of the artery past therefrom;
   d) inflating the balloon portion for a pre-determined amount of time; said inflated balloon portion deforming the atheromas immediately adjacent the outer surface of the balloon and blocking the flow of blood through said artery; and
   e) injecting into the lumen of the blocked artery prior to any ischemia through said opening in said distal catheter tip a pharmaceutically acceptable preparation including from about 10 nanomoles to about 1.0 micromole/Kg/minute of magnesium to prevent or delay ischemia.

21. The method of claim 20 wherein said pre-determined inflation time is from about two to about four minutes.

22. The method of claim 20 wherein said pre-determined inflation time is about three minutes.

23. The method of claim 20 wherein the method includes the additional steps of:
   a) deflating the balloon portion;

b) injecting a radiopaque contrast dye through said opening in said distal catheter tip into the area of atheromas narrowing;

c) performing a coronary angiogram;

d) repeating step a), b), and c) if said coronary angiogram demonstrates that said atheromas have not been sufficiently deformed; and (e) removing the catheter from the patient.

24. A method of percutaneous transluminal coronary angioplasty for treating patients having atheromatous narrowing of a coronary artery, the method including the steps of:

a) providing a multi-lumen inflatable balloon catheter, said catheter including a first lumen and second lumen, said first lumen having an inflatable balloon portion, the balloon portion having a diameter sufficient when inflated to deform the atheromas immediately adjacent its an outer surface of the balloon, said second lumen defining a conduit to a distal tip of said catheter, said distal tip located distal the inflatable balloon portion; said distal tip including an opening through which a guide wire is threaded and fluids are injected;

b) introducing said balloon catheter into the lumen of said coronary artery;

c) advancing said catheter into a portion of said coronary artery narrowed by atheromas such that the outer surface of the inflatable balloon portion is positioned immediately adjacent the atheromas narrowing the artery and the distal tip of the catheter is positioned in the lumen of the artery past therefrom;

d) inflating the balloon portion for a pre-determined amount of time from about one to about five minutes; said inflated balloon portion deforming the atheromas immediately adjacent the outer surface of the balloon and blocking the flow of blood through said artery; and e) injecting into the lumen of the blocked artery through said opening in said distal catheter tip a pharmaceutically acceptable preparation including from about 10 nanomoles to about 1.0 micromole/Kg/minute of magnesium.

* * * * *